(12) United States Patent
Pipe (10) Patent No.: US 10,429,469 B2
(45) Date of Patent: Oct. 1, 2019

(54) SYSTEM AND METHOD FOR MAGNETIC RESONANCE IMAGING USING THREE-DIMENSIONAL, DISTRIBUTED, NON-CARTESIAN SAMPLING TRAJECTORIES

(71) Applicant: Dignity Health, San Francisco, CA (US)

(72) Inventor: James G. Pipe, Phoenix, AZ (US)

(73) Assignee: DIGNITY HEALTH, San Francisco, CA (US)

( * ) Notice: Subject to any disclaimer, the term of this patent is extended or adjusted under 35 U.S.C. 154(b) by 1100 days.

(21) Appl. No.: 14/391,314

(22) PCT Filed: Mar. 27, 2013

(86) PCT No.: PCT/US2013/034148
§ 371 (c)(1),
(2) Date: Oct. 8, 2014

(87) PCT Pub. No.: WO2013/154834
PCT Pub. Date: Oct. 17, 2013

(65) Prior Publication Data
US 2015/0051479 A1    Feb. 19, 2015

Related U.S. Application Data

(60) Provisional application No. 61/686,732, filed on Apr. 11, 2012.

(51) Int. Cl.
*G01R 33/48* (2006.01)
*A61B 5/055* (2006.01)

(52) U.S. Cl.
CPC ......... *G01R 33/4818* (2013.01); *A61B 5/055* (2013.01); *G01R 33/4826* (2013.01)

(58) Field of Classification Search
CPC ......... A61B 5/00; A61B 5/055; A61B 5/0555; G01R 33/00; G01R 33/4818;
(Continued)

(56) References Cited

U.S. PATENT DOCUMENTS 4,549,140 A * 10/1985 MacFall ............... G01R 33/482
324/306
4,748,410 A * 5/1988 Macovski .......... G01R 33/4824
324/307
(Continued)

FOREIGN PATENT DOCUMENTS

WO    2008132659         11/2008
WO    WO 2008132659 A2 * 11/2008 ......... G01R 33/4824

OTHER PUBLICATIONS

Pipe, James G., et al. "A new design and rationale for 3D orthogonally oversampled k-space trajectories." Magnetic resonance in medicine 66.5 (Apr. 5, 2011): 1303-1311.*
(Continued)

*Primary Examiner* — Luther Behringer
*Assistant Examiner* — Sean D Mattson
(74) *Attorney, Agent, or Firm* — Quarles & Brady LLP (57) ABSTRACT

A system and method for sampling k-space is provided that substantially simplifies the demands placed on the clinician to select and balance the tradeoffs of a particular selected sampling methodology. In particular, the present invention provides particularly advantageous sampling methodologies that simplify the selection of a particular k-space sampling methodology and, furthermore, the tradeoffs within a particular sampling methodology.

16 Claims, 8 Drawing Sheets

(58) Field of Classification Search
CPC .............. G01R 33/482; G01R 33/4822; G01R 33/4824; G01R 33/4826

See application file for complete search history.

(56) References Cited

U.S. PATENT DOCUMENTS

| | | | | |
|---|---|---|---|---|
| 5,652,516 | A * | 7/1997 | Adalsteinsson | G01R 33/485 |
| | | | | 324/307 |
| 6,281,681 | B1 * | 8/2001 | Cline | G01R 33/54 |
| | | | | 324/307 |
| 7,206,441 | B2 | 4/2007 | Kohler | |
| 7,285,955 | B2 | 10/2007 | Roberts et al. | |
| 7,791,338 | B2 * | 9/2010 | Kim | G01R 33/561 |
| | | | | 324/307 |
| 2001/0026157 | A1 * | 10/2001 | Heid | G01R 33/4824 |
| | | | | 324/312 |
| 2003/0135105 | A1 * | 7/2003 | Jack | G01R 33/5676 |
| | | | | 600/410 |
| 2008/0045828 | A1 * | 2/2008 | Shu | G01R 33/4824 |
| | | | | 600/410 |
| 2008/0183067 | A1 | 7/2008 | Shu et al. | |
| 2008/0258727 | A1 * | 10/2008 | Qian | G01R 33/4816 |
| | | | | 324/312 |
| 2011/0095762 | A1 * | 4/2011 | Piccini | G01R 33/4824 |
| | | | | 324/312 |

OTHER PUBLICATIONS

Turley, Dallas C., and James G. Pipe. "Distributed spirals: a new class of three-dimensional k-space trajectories." Magnetic resonance in medicine 70.2 (2013): 413-419. (Year: 2013).*

The International Search Report and Written Opinion dated Jun. 25, 2013 for International Application No. PCT/EP2013/034148.

Wolfram Research, Golden Angle, Jun. 21, 2011 (Jun. 21, 2011) [retrieved on Jun. 16, 2013]. Retrieved from the Internet: <URL: http://mathworld.wolfram.com/GoldenAngle.html>. p. 1.

Chan et al., Temporal Stability of 3D-PR based on Multidimensional Golden Means: Simulation and Implementation. Proc. Intl. Soc. Mag. Reson. Med. 16, 2008. [retrieved on Jun. 16, 2013]. Retrieved from the Internet: <URL: http://cds.ismrm.org/ismrm-2008/files/01344.pdf>. p. 1344.

* cited by examiner

SYSTEM AND METHOD FOR MAGNETIC RESONANCE IMAGING USING THREE-DIMENSIONAL, DISTRIBUTED, NON-CARTESIAN SAMPLING TRAJECTORIES

CROSS-REFERENCE TO RELATED APPLICATIONS

This application represents the U.S. National Stage of International Application No. PCT/US2013/034148, filed Mar. 27, 2013 which is based on, claims priority to, and incorporates herein by reference U.S. Provisional Application Ser. No. 61/686,732, filed Apr. 11, 2012, and entitled, "SYSTEM AND METHOD FOR MAGNETIC RESONANCE IMAGING USING THREE-DIMENSIONAL, DISTRIBUTED, NON-CARTESIAN SAMPLING TRAJECTORIES."

STATEMENT REGARDING FEDERALLY FUNDED RESEARCH

N/A.

BACKGROUND OF THE INVENTION

The present disclosure relates to systems and methods for magnetic resonance imaging ("MRI"). More particularly, the present disclosure relates to systems and methods sampling k-space with three-dimensional (3D) distributed trajectories that are non-Cartesian, such as spiral and other trajectories.

When a substance such as human tissue is subjected to a uniform magnetic field (polarizing field $B_0$) applied along, for example, a z axis of a Cartesian coordinate system, the individual magnetic moments of the spins in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, Mz, may be rotated, or "tipped", into the x-y plane to produce a net transverse magnetic moment $M_t$. A NMR signal is emitted by the excited spins after the excitation signal $B_1$ is terminated, this signal may be received and processed to form an image or produce a spectrum.

The MR signals acquired with an MRI system are signal samples of the subject of the examination in Fourier space, or what is often referred to in the art as "k-space". Typically, a region to be imaged is scanned by a sequence of measurement cycles in which gradients vary according to the particular localization method being used. Each MR measurement cycle, or pulse sequence, typically samples a portion of k-space along a sampling trajectory characteristic of that pulse sequence. This is accomplished by employing magnetic fields ($G_x$, $G_y$, and $G_z$) that have the same direction as the polarizing field $B_0$, but which have a gradient along the respective x, y, and z axes. By controlling the strength of these gradients during each NMR cycle, the spatial distribution of spin excitation can be controlled and the location of the resulting NMR signals can be identified. The acquisition of the NMR signals samples is referred to as sampling k-space, and a scan is completed when enough NMR cycles are performed to adequately sample k-space. The resulting set of received NMR signals are digitized and processed to reconstruct the image using one of many well known reconstruction techniques.

In conventional, fully-sampled MRI, the number of acquired k-space data points is determined by the spatial resolution requirements, and the Nyquist criterion for the alias-free field of view (FOV). Images can be reconstructed, however, using a reduced number of k-space samples, or "undersampling". The term undersampling here indicates that the Nyquist criterion is not satisfied, at least in some regions of k-space. Undersampling is used for several reasons, including reduction of acquisition time, reduction of motion artifacts, achieving higher spatial or temporal resolution, and reducing the tradeoff between spatial resolution and temporal resolution.

Most pulse sequences sample k-space in a raster scan-like pattern sometimes referred to as a "spin-warp", a "Fourier", a "rectilinear" or a "Cartesian" scan. The time required to fully sample 3D Cartesian k-space is relatively long. This reduces the temporal resolution of time-resolved studies that acquire the same imaging volume repeatedly. Well-known undersampling methods that are used to improve the temporal resolution of such time-resolved acquisitions often focus on sampling data at the periphery of k-space less frequently than at the center because aliasing artifacts that result from undersampling are not as severe if the violation of the Nyquist criterion is restricted to the outer part of k-space.

Alternative, non-Cartesian trajectories can also provide faster sampling of k-space, and more efficient use of the gradients. When a very fast volume acquisition is required, undersampling strategies can be used in conjunction with these non-Cartesian trajectories to further reduce the scan time.

For example, "radial", or "projection reconstruction" scans, in which k-space is sampled as a set of radial sampling trajectories extending from the center of k-space, are often employed. The pulse sequences for a radial scan are characterized by the lack of a phase encoding gradient and the presence of a readout gradient that changes direction from one pulse sequence view to the next.

One such method that preserves reasonable image quality, while reducing the acquisition time by approximately half compared to a fully-sampled acquisition, is the so-called "vastly undersampled projection acquisition" or "VIPR" method, as described by Barger V A, Block W F, Toropov Y, Grist T M, Mistretta C A. Aliasing caused by undersampling in this method often can be tolerated in angiographic applications because the vessel-tissue contrast is high and the artifacts are distributed, or "spread" out in the image.

Figure 1:
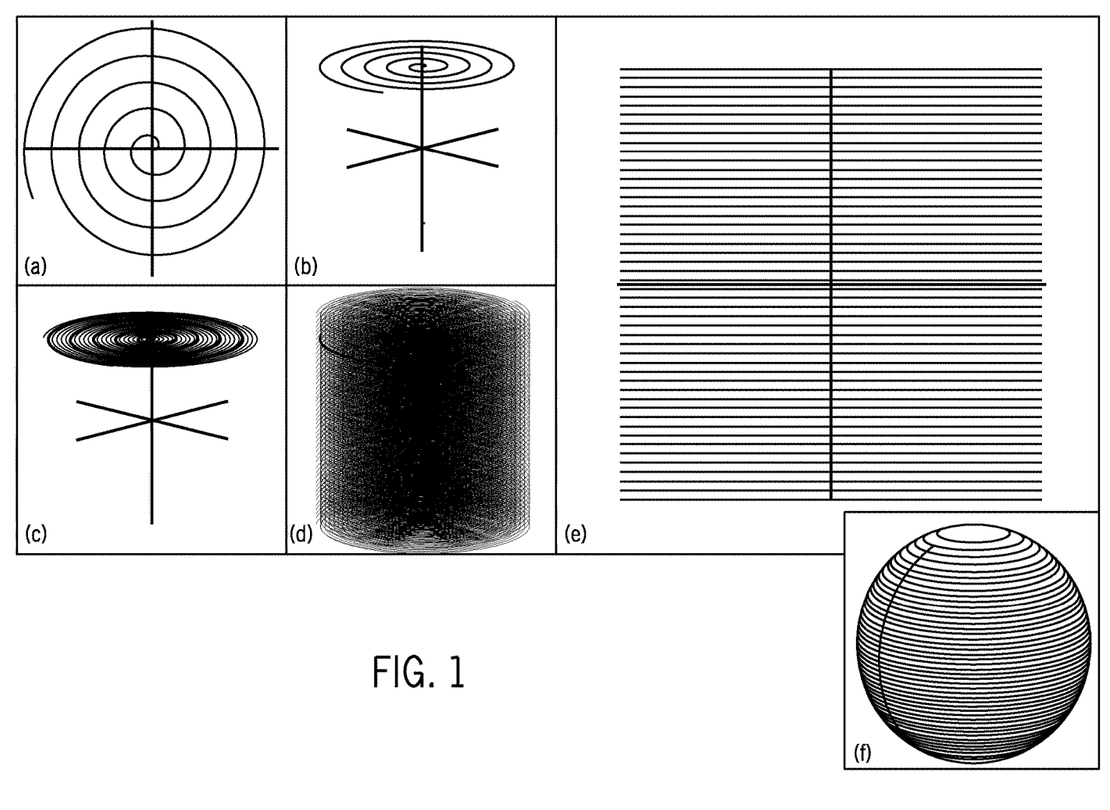
FIGS. 1A-1F are illustrations of spiral, nested spirals, stack of spirals, and spherical stack of spirals k-space sampling patterns.

Another non-Cartesian, but non-radial, sampling strategy utilizes a spiral. For example, as illustrated in FIG. 1A, the sampling pattern takes the form an Archimedean spiral that, often, begins at the center of k-space and spirals out toward the periphery of k-space. The spiral sampling pattern is non-radial because the sampling trajectory does not extend primarily in a radial direction, but curves with a primary direction that, at any given point, is approximately transverse to a radial direction and only moves radially outward or inward in a secondary direction.

As illustrated in FIG. 1B, the sampling extends in a plane that can be arranged in three-dimensional space. Furthermore, as illustrated in FIG. 1C, multiple spiral trajectories can be nested within each other to more fully sample k-space, even within a single plane. When extended to a 3D sampling, the spiral trajectory can be formed into a conventional "stack of spirals" (SOS), as illustrated in FIGS. 1D and 1E. Thus, FIGS. 1A-1E show that a 2D Archimedean spiral (FIG. 1A) can be played out in 3D k-space preceded by a phase encoding gradient to position it in a desired plane of a 3D space (FIG. 1B). Several interleafs can be placed in the same plane, but rotated uniformly to nest the samples and, thereby, fully sample that plane (FIG. 1C). These planes are then repeated at many levels along the transverse axis, forming a conventional 3D "stack of spirals" trajectory to sample a cylinder (FIG. 1D. Cutting through the plane of the axes illustrates rectangular intra-trajectory sampling (FIG. 1E).

The general SOS concept can be modified to cover a sphere using stacking planes that vary in diameter from widest at the middle to small at the top and bottom. For example, FIG. 1F shows a sphere of stacked planes in this configuration. The composite spirals that make up each plane will vary, such that there will not be just one spiral that is rotated each time. This composite spiral architecture that forms each plane, with spirals that have varied diameters between planes presents a fundamental challenge in implementing this method within the clinical setting. That is, the complex and varied sampling pattern requires substantial planning of the pulse sequence and taxing operation of the gradient systems to implement in an efficient manner without undesirable scan times.

One particular implementation of a spherical sampling method is disclosed in U.S. Pat. No. 5,532,595, which utilizes a so-called "shells" k-space sampling trajectory. In this method, a spiral pattern is sampled in k-space around a spherical surface. A complete image acquisition is comprised of a series of such spiral sampling patterns over a corresponding series of spheres of increasing diameter. The shells k-space sampling trajectory acquires 3D data on concentric spherical surfaces in k-space.

Figure 2:
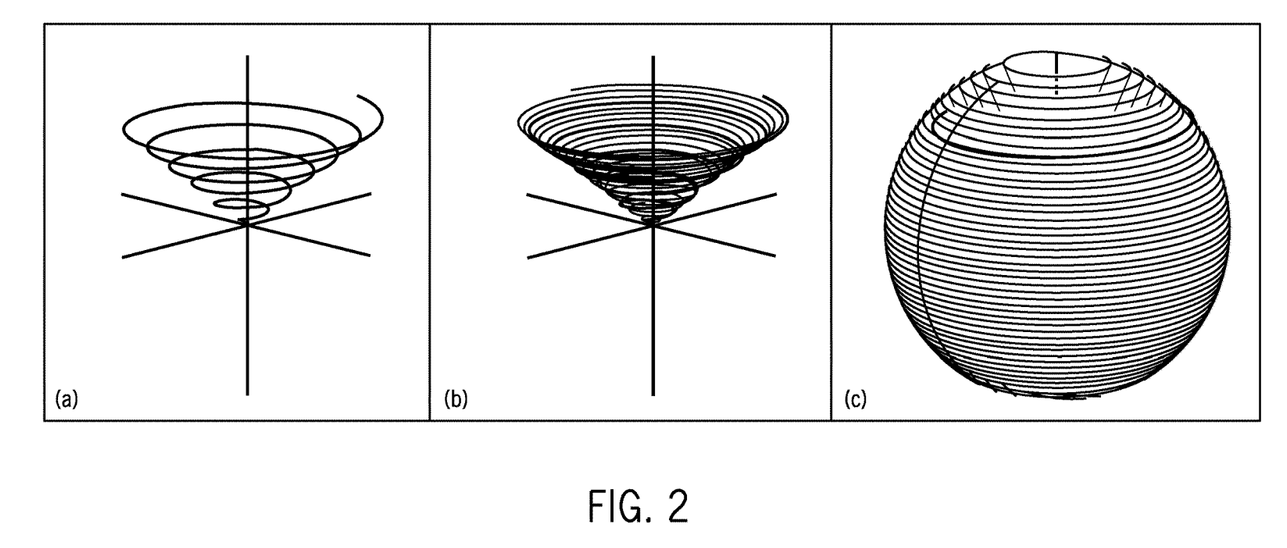
FIG. 2A-2C are illustrations of cone, nested cone and spherical stack of cone k-space sampling patterns.

Another variation or extension of the common aspects of the spiral concepts is reflected in the "stack of cones" (SOC) concept. Referring to FIG. 2A, an individual spiral can be played along a cone (starting at the center of k-space). When viewed from the vertical axis, this cone appears as a spiral and, just as described above with respect to FIG. 1, within the context of cones, multiple samplings can be nested. As illustrated in FIG. 2B, each cone is rotated about the vertical axis to fully sample a three-dimensional (3D) cone. As illustrated in FIG. 2C, multiple cones can be stacked inside each other to, thereby, sample a sphere. Like the sphere of stacked planes, the composite spirals that make up each cone will vary, such that there will not be just one cone that is rotated each time, but the cones must vary in design. This presents a fundamental challenge in implementing this method within a clinical setting.

Thus, while a number of non-Cartesian and even non-radial, 3D, sampling patters exist, each has its respective advantages and disadvantages. However, all suffer from the need to carefully plan and select imaging settings that will produce a desirable image without unacceptably long scan times. Of course, beyond careful planning of the acquisition, scan times can be reduced or at least controlled using undersampling. However, designing and implementing an undersampling strategy in conjunction with these non-Cartesian trajectories further adds complexity and extends the amount of pre-planning that is necessary, such that the requisite "homework" or pre-planning can outweigh the benefits.

Therefore, it would be desirable to have a system and method for acquiring robust sets of k-space data within a scanning duration that is clinically acceptable, but without the need for clinicians to develop extensive implementation plans to select a particular sampling methodology and balance the tradeoffs of the particular sampling methodology, such as image quality and undersampling/scan time permitted to achieve sufficient image quality for the particular clinical images desired.

SUMMARY OF THE INVENTION

The present invention overcomes the aforementioned drawbacks by providing a system and method for sampling k-space that substantially simplifies the demands placed on the clinician to select and balance the tradeoffs of a particular selected sampling methodology. In particular, the present invention provides particularly advantageous sampling methodologies that simplify the selection of a particular k-space sampling methodology and, furthermore, the tradeoffs within a particular sampling methodology.

In accordance with one aspect of the invention, a method for acquiring magnetic resonance imaging data is disclosed that includes selecting a base waveform having a trajectory extending from a center of k-space toward a periphery of k-space. Performing the base waveform using an MRI system and repeating the base waveform in a substantially consistent form. With each repetition of the base waveform, rotating the trajectory about an axis at the center of k-space by a predetermined angle to create a plurality of interleaved trajectories. In accordance with one configuration, the predetermined angle is a golden angle. Extending the repetitions along the axis to acquire k-space data in three dimensions.

In accordance with another aspect of the invention, a magnetic resonance imaging (MRI) system is disclosed including a magnet system configured to generate a polarizing magnetic field about at least a portion of a subject arranged in the MRI system and a magnetic gradient system including a plurality of magnetic gradient coils configured to apply at least one magnetic gradient field to the polarizing magnetic field. The MRI system also includes a radio frequency (RF) system configured to apply an RF field to the subject and to receive magnetic resonance signals therefrom and a computer system. The computer system is programmed to control the RF system to generate a base waveform having a trajectory extending at least one of to and from an axis located at a center of k-space and a periphery of k-space and control the RF system and the magnetic gradient system to generate a plurality of repetitions of the base waveform, each repetition of the base waveform rotationally offset by a predetermined angle about the axis with respect to adjacent repetitions of the base waveform to form a plurality of interleaved trajectories. The computer system is also programmed to control the RF system and the magnetic gradient system to generate a plurality of repetitions of the plurality of interleaved trajectories initiated from initial locations aligned along the axis to sample k-space in three dimensions.

In accordance with another aspect of the invention, a method is disclosed that includes designing, with a computer system, a pulse sequence for use with a magnetic resonance imaging (MRI) system. The pulse sequence includes a base waveform having a trajectory extending at least one of to and from an axis located at a center of k-space and a periphery of k-space and a plurality of repetitions of the base waveform, each repetition of the base waveform rotationally offset by a predetermined angle about the axis with respect to adjacent repetitions of the base waveform to form a plurality of interleaved trajectories. The pulse sequence also includes a plurality of repetitions of the plurality of interleaved trajectories initiated from initial locations aligned along the axis to sample k-space in three dimensions, wherein a cross-section of the plurality of repetitions of the plurality of interleaved trajectories extending along the axis may be mirror-symmetric. The samples along the trajectory are distributed at points with radial spacing ($k_r$) proportional to $1/\sqrt{1-kr^2}$.

In accordance with yet another aspect of the invention, a method is disclosed for controlling a magnetic resonance imaging (MRI) system to acquire medical imaging data from a subject. The method includes designing a pulse sequence having a base waveform having a trajectory to extend at least one of to and from an axis located at a center of k-space and a periphery of k-space and a plurality of repetitions of the base waveform, each repetition of the base waveform rotationally offset by a predetermined golden angle about the axis with respect to adjacent repetitions of the base waveform to form a plurality of interleaved trajectories. The pulse sequence also includes a plurality of repetitions of the plurality of interleaved trajectories initiated from initial locations aligned along the axis to sample k-space in three dimensions, wherein a cross-section of the plurality of repetitions of the plurality of interleaved trajectories extending along the axis. The method further includes performing the pulse sequence using the MRI system to collect medical imaging data of the subject and reconstructing an image of the subject from the medical imaging data.

In accordance with still another aspect of the invention, a method is disclosed for acquiring magnetic resonance imaging data. The method includes selecting a base waveform having a trajectory extending from a center of k-space toward a periphery of k-space and performing, with a magnetic resonance imaging system, the base waveform configured to acquire medical imaging data. The method also includes repeating, with the magnetic resonance imaging system, the base waveform in a substantially consistent form, with each repetition of the base waveform, rotating the trajectory about an axis at the center of k-space by a golden angle and reconstructing an image from the medical imaging data.

The foregoing and other advantages of the invention will appear from the following description. In the description, reference is made to the accompanying drawings which form a part hereof, and in which there is shown by way of illustration embodiments of the invention. Such embodiments do not necessarily represent the full scope of the invention, however, and reference is made therefore to the claims and herein for interpreting the scope of the invention.

BRIEF DESCRIPTION OF THE DRAWINGS

This patent application file contains at least one drawing executed in color. Copies of this patent or patent application publication with color drawings will be provided by the Office upon request and payment of the necessary fee.

DESCRIPTION OF THE INVENTION

Figure 3:
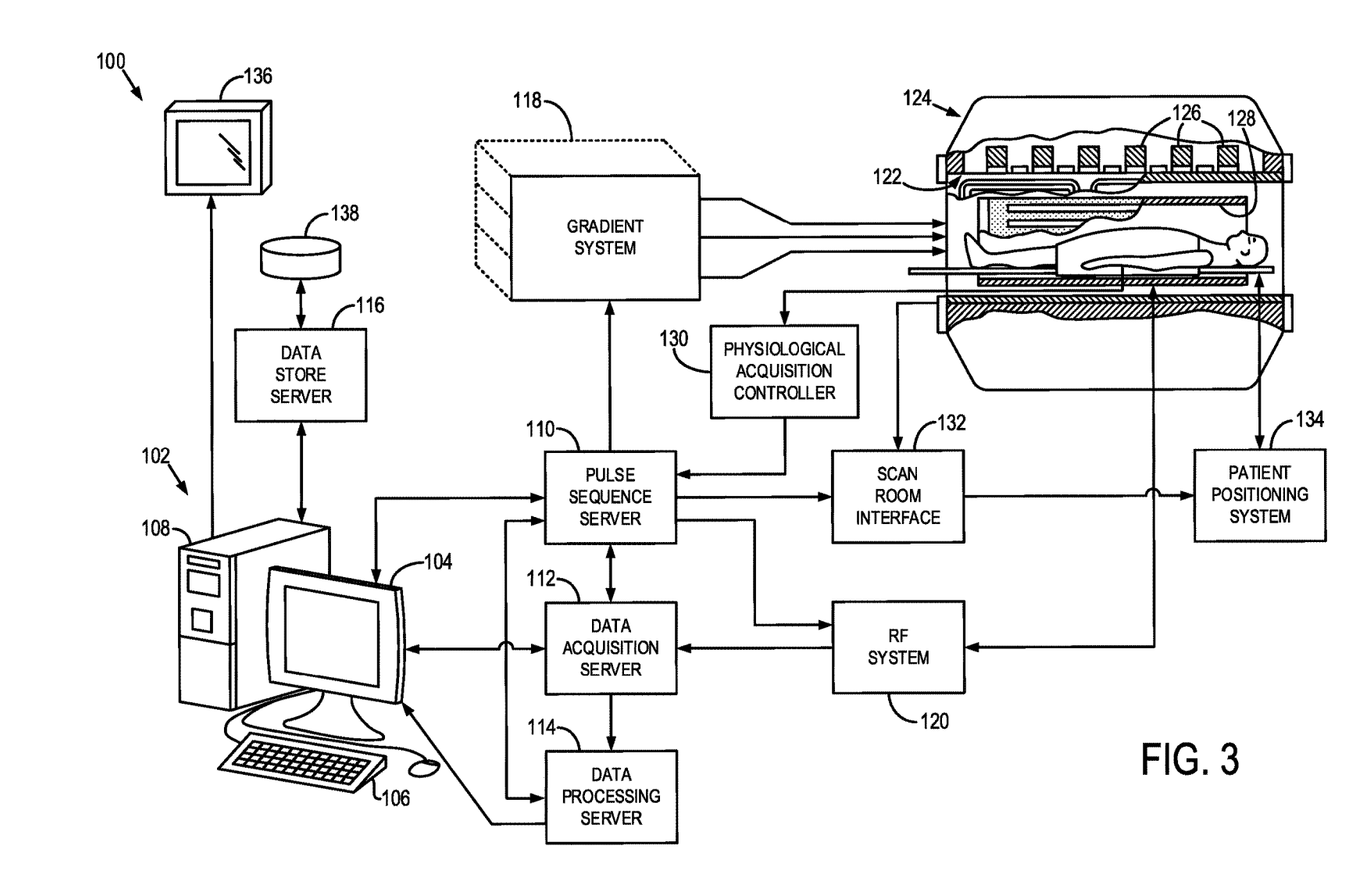
FIG. 3 is a block diagram of an exemplary magnetic resonance imaging ("MRI") system for use with the present invention.

Referring particularly now to FIG. 3, an example of a magnetic resonance imaging ("MRI") system 100 is illustrated. The workstation 102 includes a processor 108, such as a commercially available programmable machine running a commercially available operating system. The workstation 102 provides an operator interface. The workstation 102 may be designed to enable scan prescriptions to be entered into the MRI system 100. Additionally or alternatively, the workstation 102 may be a networked workstation designed for image analysis. In fact, the workstation 102 may be formed by a networked computer system that is remotely located form the MRI system 100 and is used to access images or information associated with the MRI system 100 or the like. Depending upon the configuration, the workstation 102 may be coupled to four servers: a pulse sequence server 110; a data acquisition server 112; a data processing server 114; and a data store server 116. Thus, the workstation 102 and each server 110, 112, 114, and 116 may be connected to communicate with each other.

The pulse sequence server 110 functions in response to instructions downloaded from the workstation 102 to operate a gradient system 118 and a radiofrequency ("RE") system 120. Gradient waveforms necessary to perform the prescribed scan are produced and applied to the gradient system 118, which excites gradient coils in an assembly 122 to produce the magnetic field gradients Gx, Gy, and Gz used for position encoding MR signals. The gradient coil assembly 122 forms part of a magnet assembly 124 that includes a polarizing magnet 126 and a whole-body RF coil 128.

RF waveforms are applied to the RF coil 128, or a separate local coil (not shown in FIG. 3), by the RF system 120 to perform the prescribed magnetic resonance pulse sequence. Responsive MR signals detected by the RF coil 128, or a separate local coil (not shown in FIG. 3), are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128 or to one or more local coils or coil arrays (not shown in FIG. 3).

The RF system 120 also includes one or more RF receiver channels. Each RF receiver channel includes an RF preamplifier that amplifies the MR signal received by the coil 128 to which it is connected, and a detector that detects and digitizes the I and Q quadrature components of the received MR signal. The magnitude of the received MR signal may thus be determined at any sampled point by the square root of the sum of the squares of the and components:

$$M=\sqrt{I^2+Q^2} \qquad \text{Eqn. (1);}$$

and the phase of the received MR signal may also be determined:

$$\varphi = \tan^{-1}\left(\frac{Q}{I}\right). \qquad \text{Eqn. (2)}$$

The pulse sequence server 110 also optionally receives patient data from a physiological acquisition controller 130. The controller 130 receives signals from a number of different sensors connected to the patient, such as electrocardiograph ("ECG") signals from electrodes, or respiratory signals from a bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110. Also, navigator signals may be acquired during a scan and used to adjust the operating parameters of the RF system 120 or the gradient system 118, or to control the view order in which k-space is sampled. By way of example, the data acquisition server 112 acquires MR data and processes it in real-time to produce information that may be used to control the scan.

The data processing server 114 receives MR data from the data acquisition server 112 and processes it in accordance with instructions downloaded from the workstation 102. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 114 are conveyed back to the workstation 102 where they are stored. Real-time images are stored in a data base memory cache (not shown in FIG. 3), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network to other facilities.

Figure 4:
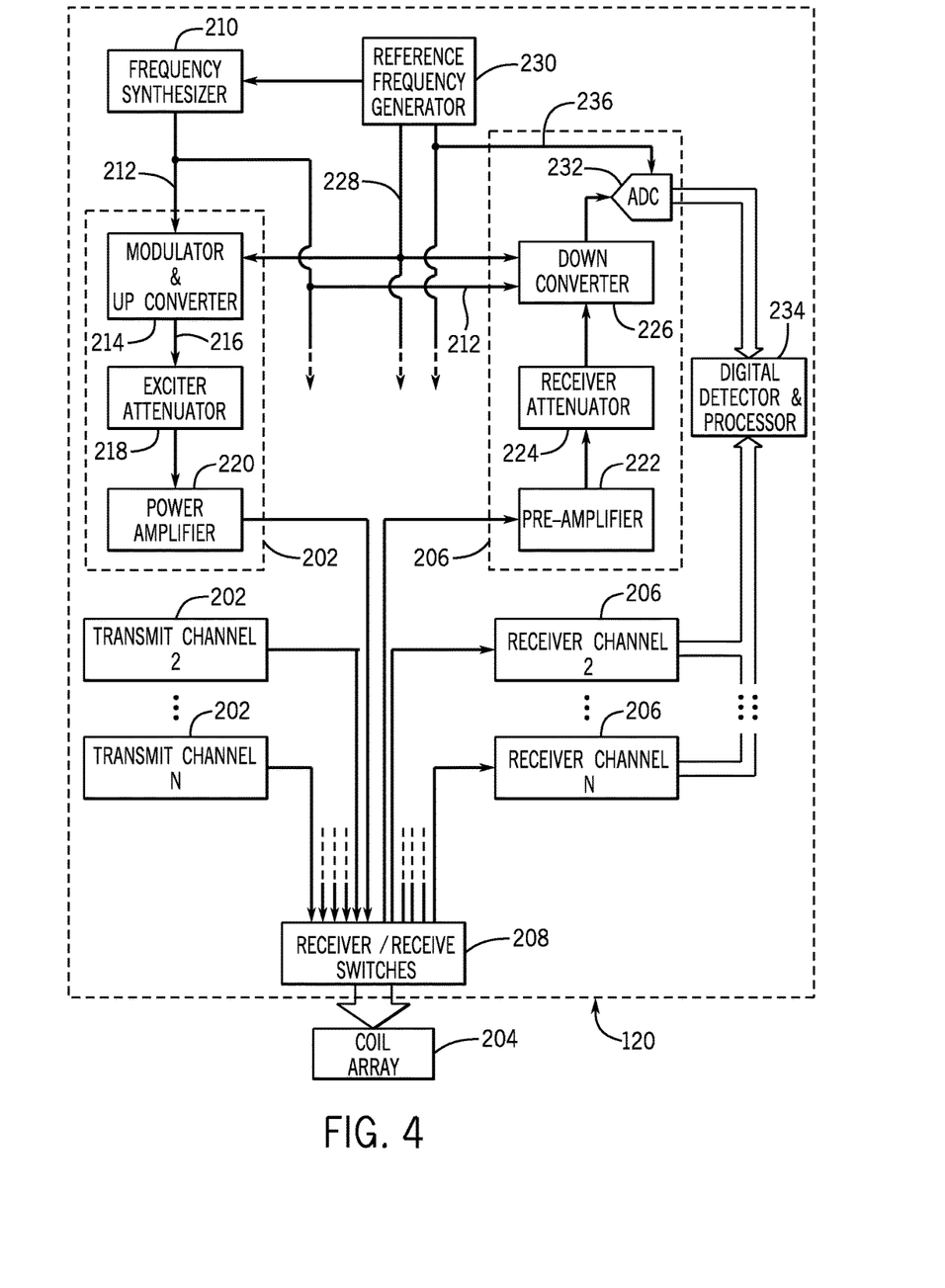
FIG. 4 is a block diagram of an example of a radio frequency ("RE") system that may form part of the MRI system of FIG. 3.

As shown in FIG. 3, the radiofrequency ("RF") system 120 may be connected to the whole body RF coil 128, or, as shown in FIG. 4, a transmission section of the RF system 120 may connect to one or more transmit channels 202 of an RF coil array 204 and a receiver section of the RF system 120 may connect to one or more receiver channels 206 of the RF coil array 204. The transmit channels 202 and the receiver channels 206 are connected to the RF coil array 204 by way of one or more transmit/receive ("T/R") switches 208. Though illustrated as having multiple transmit channels 202 and multiple receiver channels 206 connected to multiple transmit/receive switches 208, the present invention is not limited to traditional or parallel imaging systems. Also, the receiver channel 206 may also be an assembly of coils separate from the transmit coil array. In such a configuration, the T/R switches 208 are not needed. The transmit coil elements are detuned or otherwise rendered dysfunctional during the receive operation, and the receiver coil elements are similarly detuned or otherwise rendered dysfunctional during operation of the transmit coils. Such detuning may be accomplished with appropriate control logic signals.

Referring particularly to FIG. 4, the RF system 120 includes one or more transmit channels 202 that produce a prescribed RF electromagnetic field. The base, or carrier, frequency of this RF field is produced under control of a frequency synthesizer 210 that receives a set of digital signals from the pulse sequence server 110. These digital signals indicate the frequency, amplitude, and phase of the RF carrier signal produced at an output 212. The RF carrier is applied to a modulator and, if necessary, an up converter 214 where its amplitude and phase is modulated in response to a signal, R(t), also received from the pulse sequence server 110. The signal, R(t), defines the envelope of the RF pulse to be produced and is produced by sequentially reading out a series of stored digital values. These stored digital values may be changed to enable any desired RF pulse envelope to be produced.

The magnitude of the RF pulse produced at output 216 is attenuated by an attenuator circuit 218 that receives a digital command from the pulse sequence server 110. The phase of the RF pulse may also be altered using phase shifters (not shown). The modulated RF pulses are then applied to a power amplifier 220 that drives one element of the RF coil array 204, or several such elements that are electrically coupled. Multiple transmit channels then drive other elements of the multichannel transmit coil array.

The MR signal produced by the subject is picked up by the RF coil array 202 and applied to the inputs of the set of receiver channels 206. A preamplifier 222 in each receiver channel 206 amplifies the signal, which is then attenuated, if necessary, by a receiver attenuator 224 by an amount determined by a digital attenuation signal received from the pulse sequence server 110. The received signal is at or around the Larmor frequency, and this high frequency signal may be down converted in a two step process by a down converter 226. In an example of such a process, the down converter 226 first mixes the MR signal with the carrier signal on line 212 and then mixes the resulting difference signal with a reference signal on line 228 that is produced by a reference frequency generator 230. The MR signal is applied to the input of an analog-to-digital ("A/D") converter 232 that samples and digitizes the analog signal. As an alternative to down conversion of the high frequency signal, the received analog signal can also be detected directly with an appropriately fast analog-to-digital ("A/D") converter and/or with appropriate undersampling. The sampled and digitized signal may then be applied to a digital detector and signal processor 234 that produces in-phase (I) and quadrature (Q) values corresponding to the received signal. The resulting stream of digitized I and Q values of the received signal are output to the data acquisition server 112. In addition to generating the reference signal on line 228, the reference frequency generator 230 also generates a sampling signal on line 236 that is applied to the A/D converter 232.

As described above, there are a variety of k-space sampling strategies, with two of the most common or fundamental strategies being referred to as 1) a "spin-warp", a "Fourier", a "rectilinear," or a "Cartesian" scans and 2) "radial" or "projection" scans. Also, there are non-Cartesian, non-radial scans, such as spirals. When extending these concepts into three dimensions, the spiral scans can be stacked into a stack of spirals (SOS) or spherical stack of spirals (SSOS), or extended along the third dimension into a cone or stack of cones (SOC). However, each of these non-Cartesian, non-radial sampling strategies has substantial drawbacks, including requiring substantial scan pre-planning or preparation or extended scan durations. A more specific list of features and drawbacks of the above-referenced sampling strategies follows in Table 1.

by cutting through the CDSI along a plane extending along the transverse axis 504 to reveal an intra-trajectory sampling in the cut plane that may be mirror-symmetric about the transverse axis 504. As illustrated best in FIG. 5E, the spacing between trajectories may be uniform or substantially uniform.

Thus, a k-space sampling strategy is provided with a variety of advantageous features not available together in traditional Cartesian and radial samplings. First, the sampling strategy utilizes a starting point on or proximate to the transverse axis and for each interleaf the starting point is spaced at regular or near-regular intervals along the transverse axis from a neighboring interleaf. The trajectories are rotated about the transverse axis by a constant or near-constant increment with respect to neighboring trajectories. Preferably, the rotation angle is the golden angle, which is 180 degrees*multiplied by the quantity of three less than the square root of 5, or approximately 137.5 degrees. The interleafs are based off of a single waveform (referred to as the base waveform), with no or little modification other than rotation or scaling.

Figure 7:
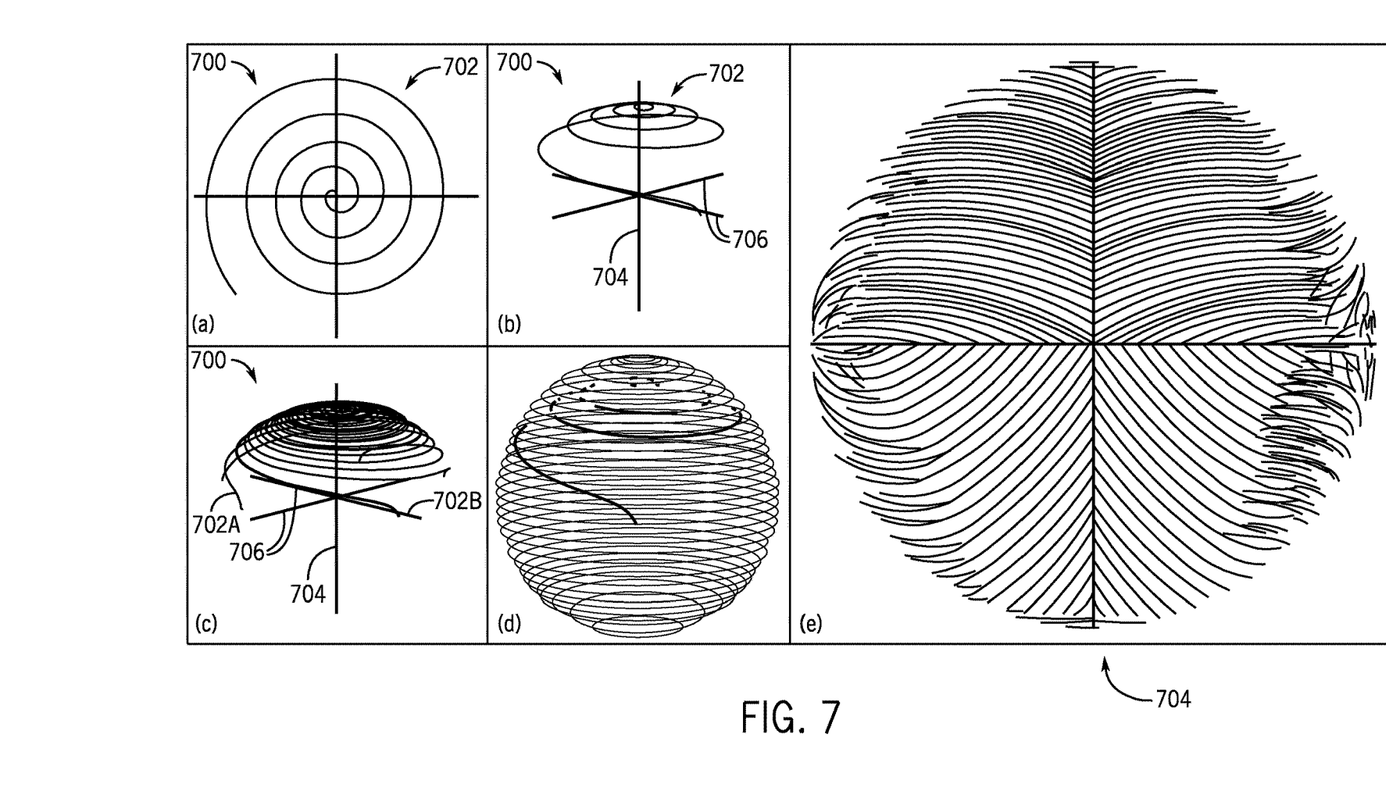
FIGS. 7A-7E are a series of representations of a spherical distributed spiral interleafs (SDSI) k-space sampling strategy for use with the MRI system of FIGS. 3 and 4 in accordance with the present invention.

Within this construct, additional sampling schemes are contemplated. For example, one sampling scheme 700, referring to FIG. 7A, utilizes a base 2D spiral 702 that is

TABLE 1

| Trajectory | Volume Covered | Base Spiral Waveform | No. of Non-Cartesian Directions | No. of Blurring Directions | Near-Optimal Speed | Near-Optimal SNR Efficiency |
| --- | --- | --- | --- | --- | --- | --- |
| SOS | Cylinder | 1 | 2 | 2 | Yes | Yes |
| SSOS | Sphere | Many | 2 | 3 | Yes | Yes |
| SOC | Sphere | Many | 3 | 3 | No | No |

Figure 5:
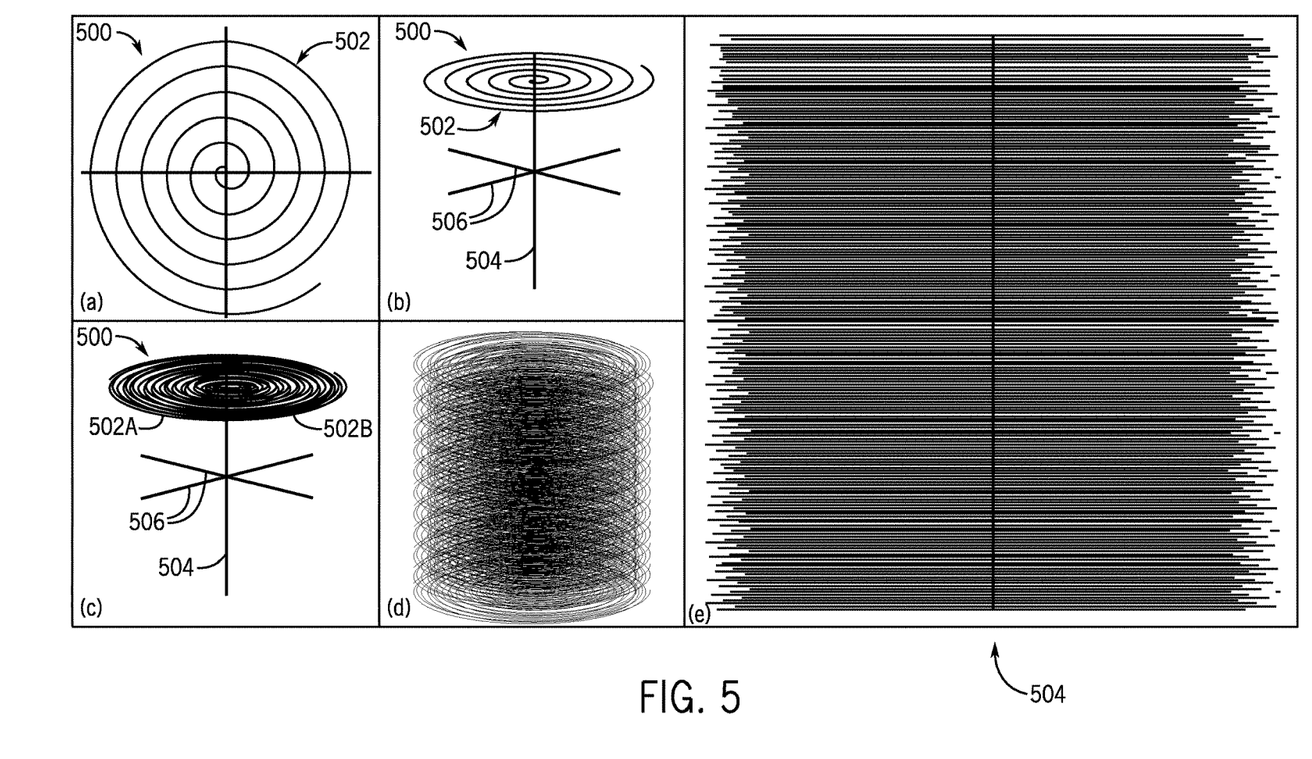
FIGS. 5A-5E are a series of representations for creating a cylindrical distributed spiral interleafs (CDSI) k-space sampling strategy for use with the MRI system of FIGS. 3 and 4 in accordance with the present invention.

Referring now to FIGS. 5A and 5B, a sampling scheme 500 is illustrated that is formed using a 2D Archimedean spiral 502 be played out in 3D k-space preceded by a phase encoding gradient to position the Archimedean spiral 502 along an axis 504 transverse to a plane 506 of the Archimedean spiral 502. Referring to FIG. 5C, the Archimedean spiral 502 is repeated to form N interleafs 502A, 502B . . . 502N that are each placed at a different location along the transverse axis 504 (span/N apart), and rotated by, for example, the "golden angle" from their neighboring Archimedean spiral 502.

Figure 6:
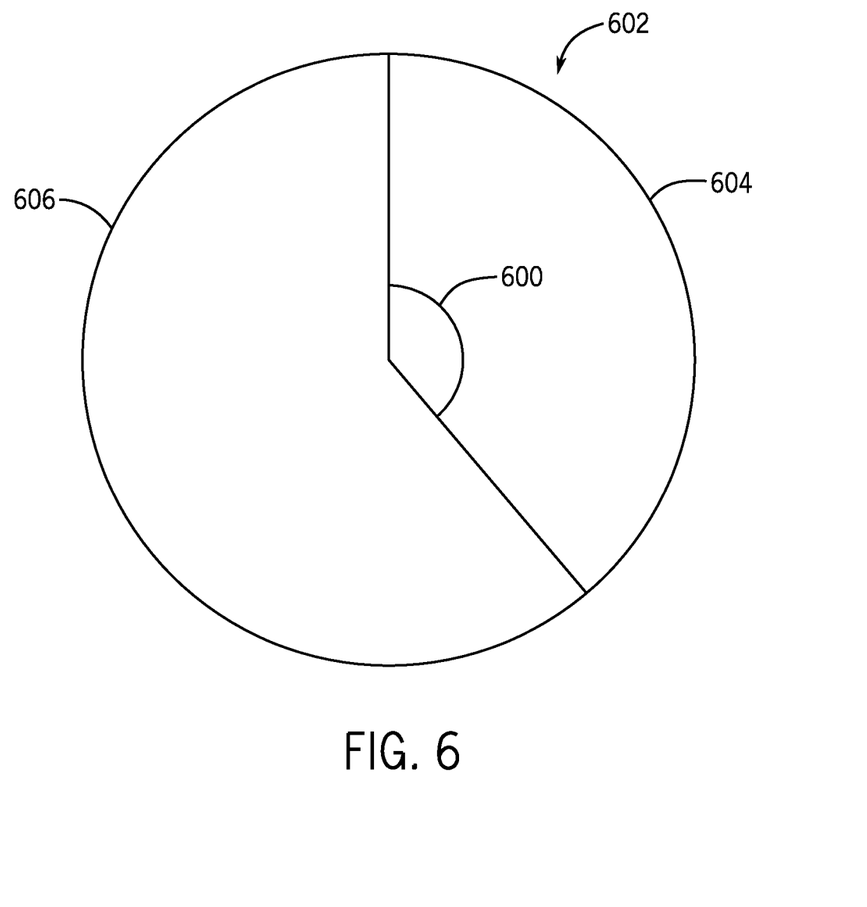
FIG. 6 is a schematic illustration of a "golden angle".

Referring to FIG. 6, the "golden angle" is an angle 600 formed when sectioning the circumference of a circle 602 into two arcs 604, 606 such that a ratio of a length of a larger of the arcs 606 to a length of a smaller of the arcs 604 is the same as a ratio of a circumference of the circle 602 to the length of the larger arc 606. In this creation of a "golden section" by the shorter arc 604 and longer arc 606, the "golden angle" 600 is the smaller of the angles created by the sectioning of the circle 602. Algebraically, the relationship is expressed as follows:

$$\frac{a+b}{a} = \frac{a}{b}. \quad \text{Eqn. (3)}$$

Mathematically, the golden angle is then the angle 600 subtended by the smaller arc 604 of length 606. It measures approximately 137.508 degrees, or about 2.39996 radians.

Referring to FIG. 5C-5E, the interleafs 502A, 502B . . . 502N for a continuous 3D cylindrical distributed spiral interleafs (CDSI) sampling strategy can be best understood played out with a desired radial density. Referring to FIG. 7B, the same spiral is played out in 3D k-space preceded by a phase encoding gradient to position it along a transverse axis 704, and with a concurrent transverse (for example z) gradient during readout to make sampling in the transverse direction follow the surface of a sphere. Referring to FIG. 7C, N interleafs 702A, 702B . . . 702N are each placed at a different location along the transverse axis 704 (span/N apart), and rotated by the golden angle from neighboring interleafs. As illustrated in FIG. 7D, the N interleafs 702A, 702B . . . 702N form a continuous 3D spherical distributed spiral interleafs (SDSI) sampling scheme. Referring to FIG. 7E, cutting through the transverse plane 704 again illustrates the intra-trajectory sampling in the cut plane, which may be mirror-symmetric about the transverse axis. As illustrated in FIG. 7E, the spacing between trajectories may be uniform or generally uniform.

By way of example, assuming the above-described transverse direction is the z-direction, the kz portion of the trajectories 702A, 702B . . . 702N are curved to create a desired shape, which is generally circularly symmetric about the transverse (or, by way of this example, kz) axis. This, along with the initial spacing of interleafs determines a kz sampling density as the neighboring planes are bent towards each other. The kz density may vary throughout k-space. The radial kx-ky spacing of the base waveform is set equal or nearly equal to the desired density (which may be constant or may vary throughout k-space) divided by the local kz density. This process can be imagined as a rotational extrusion of a 2D shape about the kz axis, where the 2D shape is determined by the function defining kz with respect to kx-ky.

Figure 8:
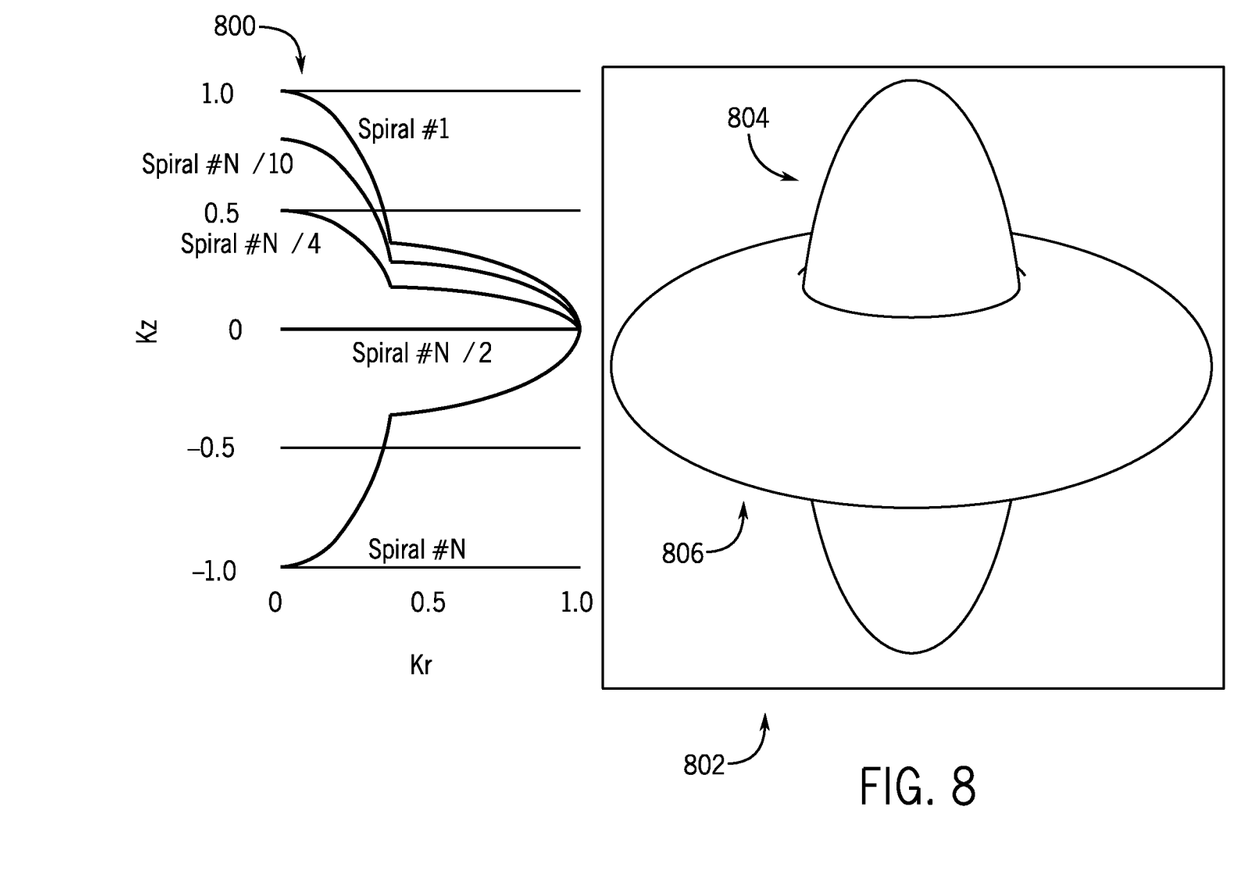
FIG. 8 is a graph and graphical representation of a dual-ellipsoid distributed spiral interleafs (DSI) k-space sampling strategy for use with the MRI system of FIGS. 3 and 4 in accordance with the present invention.

Referring now to FIG. 8, these concepts can be further extended. Specifically, change in kz can be controlled as a function of radial k-space location in kx-ky, such that kr is equal to the square root of the sum of kx squared and ky squared. As illustrated in FIG. 8, the kz-kr relationship can be predefined, for example, as illustrated by graph 800. Using the relationships between kz and kr as defined in the graph, the a k-space sampling strategy can be created based on the principles described above with respect to FIG. 7, yet having the overall architecture illustrated by k-space sampling pattern 802, which can be conceived of as having a vertical component 804 extending transverse to a horizontal component 806. The data, collected in a single scan, can be particularly advantageous for, for example, creating a set of high-resolution axial scans, from the horizontal part 806 of the trajectory, as well as coronal and/or sagittal scans that have high resolution in the vertical direction, from the elongated vertical part 804 of the trajectory.

The above-described golden spherical stack of spirals (GSSOS) sampling scheme can be envisioned in a variety of ways. For example, it can be envisioned as an example of how a 2D shape can be rotationally extruded. On the other hand, it can be modeled or otherwise envisioned in a mathematical construct. For example, the scheme can be considered as a set of trajectories that begin at equally spaced locations along the transverse axis. For discussion purposes, assume that the transverse axis is kz and, thus, the equally spaced locations along kz are represented by $kz_0(n)$ and the non-transverse plane extends along kx-ky with samples distributed radially in the kx-ky plane, where kr is the radial k-space location in kx-ky. Within this example, the trajectories can be modeled as:

$$kr = \sqrt{kx^2 + ky^2} \quad \text{Eqn. (4)};$$

where kr is zero at the kz axis and 1 at the farthest periphery of k-space that is sampled (e.g., the "equator" of the sphere). Then, radial spacing $$\left(\frac{dkr}{d\theta}\right)$$

is proportional to $1/\sqrt{1-kr^2}$, such that $$kz = kz_0(n) * \sqrt{1-kr^2} \quad \text{Eqn. (5)}.$$

Table 2 provides some additional detail regarding the advantageous features of the above-described sampling patterns.

TABLE 2

| Trajectory | Volume Covered | Base Spiral Waveform | No. of Non-Cartesian Directions | No. of Blurring Directions | Near-Optimal Speed | Near-Optimal SNR Efficiency |
|---|---|---|---|---|---|---|
| GSOS | Cylinder | 1 | 3 | 2 | Yes | Yes |
| GSSOS | Sphere | 1 | 3 | 2 | Yes | Yes |

With respect to the volume covered, data can be sampled from many different volumes in k-space. Measuring data over spheres is generally better than measuring it over cylinders, which in turn is generally better than measuring over cubes, which done for Cartesian-based sampling. This is true because more isotropic resolution is provided by the above-described samplings and a better-behaved point spread function is achieved. The latter feature creates "Gibbs ringing" or "Truncation artifact" in many conventional methods, and is far more prominent for images generated from cubic data volumes and images generated from cylindrical data volumes in the transverse direction. Notably, for all of the above-described methods, the aspect ratio can be readily changed, for example, by collecting a ellipsoid instead of a sphere.

With respect to the base waveform, the present schemes advantageously utilize a base spiral waveform with a consistent shape. Implementing a method in practice is far easier if it is based on a single spiral waveform. Spherical stack of spirals (SSOS) and stack of cones (SOC) requires one to calculate many spiral waveforms, generally requiring some approximations to the actual waveform played out. The present invention overcomes such problems by using a consistent or singular base spiral waveform, but in a manner that enables 3D samplings.

For SOS and SSOS, data sampling in the transverse direction described above (e.g., the "z" direction) is in a regular pattern. That is, the sampling along the transverse direction is Cartesian sampling. As such, SOS and SSOS suffer from the inherent drawbacks of Cartesian sampling. GSOS and GSSOS achieve the advantageous described herein and, in addition, avoid Cartesian sampling patters, even in a single direction.

A substantial challenge to non-Cartesian and non-radial sampling methods is image blurring, which occurs in areas where the magnetic field is not uniform, causing so-called spin "off-resonance". Off-resonance blurring will happen in directions for which the sampling time in k-space is not constant. For SOS, CDSI, and SDSI, the sampling time in the transverse direction (assume, kz), for any location in the basic non-transverse plane (assume kx, ky), is constant. Accordingly, blurring only occurs in the directions along the non-transverse plane (e.g., x and y directions). For all of the other methods, blurring happens in all three directions. Methods to correct this will be compromised by this fact, and the computational burden will increase greatly.

As for scan duration, the use of CDSI and SDSI trajectories requires scan trajectories of roughly the same duration as SOS and SSOS, as indicated in Table 1. However, the CDSI and SDSI trajectories, as addressed above, have an advantageous number of blurring directions, like SOC, but do not suffer from the inefficiencies of the SOC trajectory caused by heavily oversampled in the middle of k-space.

Likewise, SDSI and CDSI provide advantageous signal-to-noise ratio (SNR) efficiencies, which is related to sampling density, and is optimal when the sampling density is uniform. This is more-or-less equivalent for all methods except SOC, which is heavily oversampled in the middle of k-space.

Therefore, the above-described systems and methods provide means of sampling trajectories that start from or near a single axis, referred to herein as a transverse axis, for example, as may be implemented as kz, but it could be any direction. The starting point of the trajectories on the transverse axis are spaced at regular or near-regular intervals. The trajectories are rotated about the transverse axis by a constant or near-constant increment with respect to neighboring trajectories. Preferably, the rotation angle is the golden angle, or approximately 137.5 degrees.

The trajectories utilize the concept of a single base waveform, with no or little modification other than rotation and/or scaling throughout the samplings. The transverse portion of the trajectories are curved to create a desired shape, which is generally circularly symmetric about the transverse axis. This, along with the initial spacing described above determines a transverse sampling density as the neighboring planes are bent towards each other. The transverse sampling density may vary throughout k-space. The radial spacing within the base waveform is set equal or nearly equal to the desired density, which may be constant or may vary throughout k-space, divided by the local transverse sampling density. This process can be imagined as a rotational extrusion of a 2D shape about the transverse axis, where the 2D shape is determined by the function defining transverse sampling with respect to sampling in the non-transverse plane.

The start and end of the trajectories may be reversed, or may be traversed in some other way. In one configuration, the cylindrical distributed spiral interleafs has no curve along the transverse axis and equal spacing, and if a uniform sampling density throughout k-space is desired, then the base waveform may be an Archimedean spiral with uniform radial spacing. In another configuration, the distributed spiral interleafs, trajectories begin at equally spaced locations k(n) along the transverse axis. The trajectories then follow a general path that can be mathematically described or selected based on a modeling function The present invention has been described in terms of one or more preferred embodiments, and it should be appreciated that many equivalents, alternatives, variations, and modifications, aside from those expressly stated, are possible and within the scope of the invention. Therefore, the invention should not be limited to a particular described embodiment.

The invention claimed is:

1. A magnetic resonance imaging (MRI) system, comprising:
   a magnet system configured to generate a polarizing magnetic field about at least a bore of the MRI system that is configured to receive a subject to be imaged;
   a magnetic gradient system including a plurality of magnetic gradient coils configured to apply at least one magnetic gradient field to the polarizing magnetic field;
   a radio frequency (RF) system configured to apply an RF field to the subject and to receive magnetic resonance signals therefrom;
   a computer system programmed to:
   control the RF system to generate a base waveform having a trajectory beginning at an axis located at a center of k-space and extending to a periphery of k-space or beginning at the periphery of k-space and extending to end sampling at the axis located at the center of k-space;
   control the RF system and the magnetic gradient system to generate a plurality of repetitions of the base waveform, each repetition of the base waveform rotationally offset by a predetermined angle about the axis with respect to adjacent repetitions of the base waveform to form a plurality of interleaved trajectories;
   control the RF system and the magnetic gradient system to generate a plurality of repetitions of the plurality of interleaved trajectories initiated from locations aligned along the axis to sample k-space in three dimensions, wherein a cross-section of the plurality of repetitions of the plurality of interleaved trajectories extending along the axis is mirror-symmetric;
   wherein samples along the trajectory are distributed at points with radial spacing $$\left(\frac{dk_r}{d\theta}\right)$$

proportional to $1/\sqrt{1-k_r^2}$ such that a given k-space location (k) is given by $k=k_0(n)*\sqrt{1-k_r^2}$, where $k_0$ is an initial k-space sampling location along the trajectory and n is a number incremented with each sampling along the trajectory.

2. The system of claim 1 wherein the predetermined angle is a golden angle.

3. The system of claim 1 wherein the predetermined angle is equal to 180 degrees multiplied by a quantity of three less than the square root of 5 degrees.

4. The system of claim 1 wherein the trajectory includes a two-dimensional (2D) Archimedean spiral.

5. The system of claim 1 wherein the locations along the trajectory with respect to the axis are selected as a function of radial k-space location in a transverse plane to the axis, such that $k_r$ is equal to a square root of a sum of a first distance in the transverse plane from the axis squared and second distance in the transverse plane from the axis squared, wherein the first and second distances are determined along lines orthogonal to each other.

6. The system of claim 1 wherein the plurality of repetitions of the base waveform occur during application of a phase encoding gradient to extend the trajectory in a direction oriented along the axis.

7. The system of claim 6 wherein the plurality of repetitions of the plurality of interleaved trajectories occurs during application of a concurrent transverse phase encoding gradient to move the locations to cause the periphery of k-space to follow a surface of a sphere.

8. A method comprising:
   designing, with a computer system, a pulse sequence for use with a magnetic resonance imaging (MRI) system comprising:
   a base waveform having a trajectory beginning at an axis located at a center of k-space and extending to a periphery of k-space or beginning at the periphery of k-space and extending to end at the axis located at the center of k-space;
   a plurality of repetitions of the base waveform, each repetition of the base waveform rotationally offset by a predetermined angle about the axis with respect to adjacent repetitions of the base waveform to form a plurality of interleaved trajectories;
   a plurality of repetitions of the plurality of interleaved trajectories initiated from locations aligned along the axis to sample k-space in three dimensions, wherein a cross-section of the plurality of repetitions of the plurality of interleaved trajectories extending along the axis is mirror-symmetric;
   wherein samples along the trajectory are distributed at points with radial spacing $$\left(\frac{dk_r}{d\theta}\right)$$

proportional to $\sqrt{1-k_r^2}$, such that a given k-space location (k) is given by $k=k_0(n)*\sqrt{1-k_r^2}$, where $k_0$ is an initial k-space sampling location along the trajectory and n is a number incremented with each sampling along the trajectory.

9. The method of claim 8 wherein the predetermined angle is a golden angle.

10. The method of claim 8 wherein the predetermined angle is equal to 180 degrees multiplied by a quantity of three less than the square root of 5 degrees.

11. The method of claim 8 wherein the trajectory includes a two-dimensional (2D) Archimedean spiral.

12. The method of claim 8 wherein locations along the trajectory with respect to the axis are selected as a function of radial k-space location in a transverse plane to the axis, such that $k_r$ is equal to a square root of a sum of a first distance in the transverse plane from the axis squared and second distance in the transverse plane from the axis squared, wherein the first and second distances are determined along lines orthogonal to each other.

13. The method of claim 8 wherein the plurality of repetitions of the base waveform occur during application of a phase encoding gradient to extend the trajectory in a direction oriented along the axis.

14. The method of claim 13 wherein the plurality of repetitions of the plurality of interleaved trajectories occur during application of a concurrent transverse phase encoding gradient to move the locations to cause the periphery of k-space to follow a surface of a sphere.

15. A method for controlling a magnetic resonance imaging (MRI) system to acquire medical imaging data from a subject, the method comprising:

designing a pulse sequence comprising a base waveform having a trajectory beginning at an axis located at a center of k-space and extending to a periphery of k-space or beginning at the periphery of k-space and extending to end at the axis located at the center of k-space;

a plurality of repetitions of the base waveform, each repetition of the base waveform rotationally offset by a predetermined golden angle about the axis with respect to adjacent repetitions of the base waveform to form a plurality of interleaved trajectories;

a plurality of repetitions of the plurality of interleaved trajectories initiated from locations aligned along the axis to sample k-space in three dimensions, wherein a cross-section of the plurality of repetitions of the plurality of interleaved trajectories extending along the axis;

wherein samples along the trajectory are distributed at points (k) with radial spacing;

performing the pulse sequence using the MRI system to collect medical imaging data of the subject;

and reconstructing an image of the subject from the medical imaging data, wherein samples along the trajectory are distributed at points with radial spacing $$\left(\frac{dk_r}{d\theta}\right)$$

proportional to $\sqrt{1-k_r^2}$, such that a given k-space location (k) is given by $k=k_0(n)*\sqrt{1-k_r^2}$, where $k_0$ is an initial k-space sampling location along the trajectory and n is a number incremented with each sampling along the trajectory.

16. The method of claim 15 wherein the predetermined golden angle is equal to 180 degrees multiplied by a quantity of three less than the square root of 5 degrees.

* * * * *

UNITED STATES PATENT AND TRADEMARK OFFICE
CERTIFICATE OF CORRECTION

PATENT NO. : 10,429,469 B2
APPLICATION NO. : 14/391314
DATED : October 1, 2019
INVENTOR(S) : James G. Pipe Page 1 of 1

It is certified that error appears in the above-identified patent and that said Letters Patent is hereby corrected as shown below:

In the Specification

Column 5, Line 64, "RE" should be --RF--.

Column 6, Line 36, "RE" should be --RF--.

Signed and Sealed this
Seventeenth Day of March, 2020

Andrei Iancu
*Director of the United States Patent and Trademark Office*